US00PP10282P

United States Patent [19]

Zary

[11] Patent Number: Plant 10,282

[45] Date of Patent: Mar. 17, 1998

[54] FLORIBUNDA ROSE PLANT NAMED 'JACMENT'

[75] Inventor: Keith W. Zary, Thouand Oaks, Calif.

[73] Assignee: Bear Creek Gardens, Inc,, Medford, Oreg.

[21] Appl. No.: 764,733

[22] Filed: Dec. 3, 1996

[51] Int. Cl.[6] ..... A01H 5/00

[52] U.S. Cl. ..... Plt./22

[58] Field of Search ..... Plt./22, 11

[56] References Cited

U.S. PATENT DOCUMENTS

P.P. 2,150 5/1962 Begonia et al. ..... Plt./22

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class having large flowers; a well-branched, upright growth habit; glossy, dark green, leathery foliage; resistance to powdery mildew and rust; and an old-fashioned open flower.

1 Drawing Sheet

The present invention relates to a new and distinct variety of rose plant of the floribunda class which was originated by me crossing an unnamed seedling with the variety JACient, U.S. Plant Pat. No. 6,725.

The primary objective of this breeding was to produce a new rose variety having the attractive coral pink and white blend flower color and the bushy floribunda habit of the female parent combined with the dark green, leathery, disease resistant foliage and large flowers of the male parent. The objective was substantially achieved, along with other desirable improvements, as evidenced by the following unique combination of characteristics that are outstanding in the new variety and that distinguish it from its parents, as well as from all other varieties of which I am aware:

1. An old-fashioned appearance to the open flower;
2. Dark green, leathery foliage;
3. Resistance to powdery mildew and rust;
4. Upright, well branched floribunda habit of growth; and
5. Large flowers for a floribunda.

Asexual reproduction of this new variety by budding, as performed at Wasco, Calif., shows that the foregoing and all other characteristics and distinctions come true to form and are established and transmitted through succeeding propagations.

The accompanying illustration shows tpical specimens of the vegetative growth and flowers of this new variety in different stages of development, depicted in color as nearly true as it is reasonably possible to make the same in a color illustration of this character.

The following is a detailed description of my new rose cutivar with color descriptions using terminology in accordance with The Royal Horticultural Society (London) Colour Chart, except where ordinary dictionary significance of color is indicated.

Parentage:

*Seed parent.*—An unnamed seedling.

*Pollen parent.*—JACient.

Classification:

*Botanical.*—*Rosa hybrida.*

*Commercial.*—Floribunda.

FLOWER

Observations made from specimens grown in a garden environment at Somis, Calif., in March through September, 1996.

Blooming habit: Recurrent.

Bud:

*Size.*—1½ inches long when the petals start to unfurl.

*Form.*—The bud form is long, pointed ovoid.

*Color.*—When sepals first divide, bud color is Yellow Orange Group 20D but, as sepals divide, color changes quickly with exposure to sunlight to Red Group 46B. When half blown, the flower center is Yellow Orange Group 20D with petal outer edges tipped in Red Group 46B; and the lower sides of the petals are Yellow Orange Group 20D.

*Sepals.*—Color: Green Group 138C, and often reddish brown where exposed to sun. Surface texture: Covered in fine hairs. There are three normally to heavily appendaged sepals. There are two unappendaged sepals with hairy edges.

*Receptacle.*—Color: Green Group 137D. Shape: Funnel. Size: Medium (⅜ inch×⅜ inch). Surface Smooth.

*Peduncle.*—Length: Short (2 inches). Surface: Smooth. Color: Light green and can be bronzy. Strength: Stiff, erect.

Bloom:

*Size.*—Large. Average open size is 4 inches.

*Borne.*—Singly, several together, in flat clusters of 3 to 5 flowers.

*Stems.*—Short. Average length is about 12 inches to 14 inches.

*Form.*—When first open: High centered. Permanence: Flattens somewhat, outer petals curl back while inner petals can fold or recurve.

*Petalage.*—Number of petals under normal conditions: 30 to 35.

*Color.*—The upper side of the petals is Yellow Orange Group 20D except on petal edges where it is Red Group 46B. The reverse side of the petals is Yellow Orange Group 20D. The base of each petal has a small yellow (Yellow Group 6B) half moon (¼ inch×¼ inch) at the point of attachment. The major color on the upper side is Yellow Orange Group 20D.

*Variegations.*—None.

*Discoloration.*—The general tonality at the end of the first day: Little change. At the end of the third day: Petal edges have turned to Red Group 46D. By day five, much of the petal exposed to sunlight has turned color to Red group 46B. By day six, this color fades to Red Group 46C then 46D.

*Fragrance.*—Moderate.

Petals:

*Texture.*—Thick.

*Shape.*—Round.

*Form.*—Tips slightly recurved on the outer petals. The inner petals are often recurved or folded.

*Arrangement.*—Imbricated, with few petaloids in the center.

*Persistence.*—Drop off cleanly.

*Lastingness.*—On the plant: Long (6 days). As a cut flower: Long (8 days to 9 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon Yellow.

*Styles.*—Color: Yellow.

*Stigmas.*—Color: Yellow.

Form: Bush.

Growth: Vigorous; upright; branching; height at one year without pruning is 4 feet, and width at one year without pruning is 3 feet (in Southern California).

Foliage:

*Number of leaflets on normal mid-stem leaves.*—5.

*Size.*—Medium (5 inches×4 inches).

*Quantity.*—Abundant.

*Color.*—New foliage: Upper and lower surface Greyed Orange Group 176A but quickly turning green. Old foliage: Upper surface Green Group 137A. Lower surface Green Group 138B.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Rough, with prickles and glands.

*Stipules.*—Medium (5/38 inch), serrated.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Many.

*Form.*—Medium (3/8 inch), straight.

*Color when young.*—Red.

Small prickles:

*Quantity.*—On main stalks: Few. On laterals: Many.

*Color.*—Brown when mature; red when young.

I claim:

1. A new and distinct variety of rose plant of the floribunda class, substantially as herein shown and described, characterized particularly as to novelty by the unique combination of its large flowers; its well branched, upright growth; its glossy, dark green, leathery foliage; its resistance to powdery mildew and rust; and its old-fashioned open flower.

* * * * *

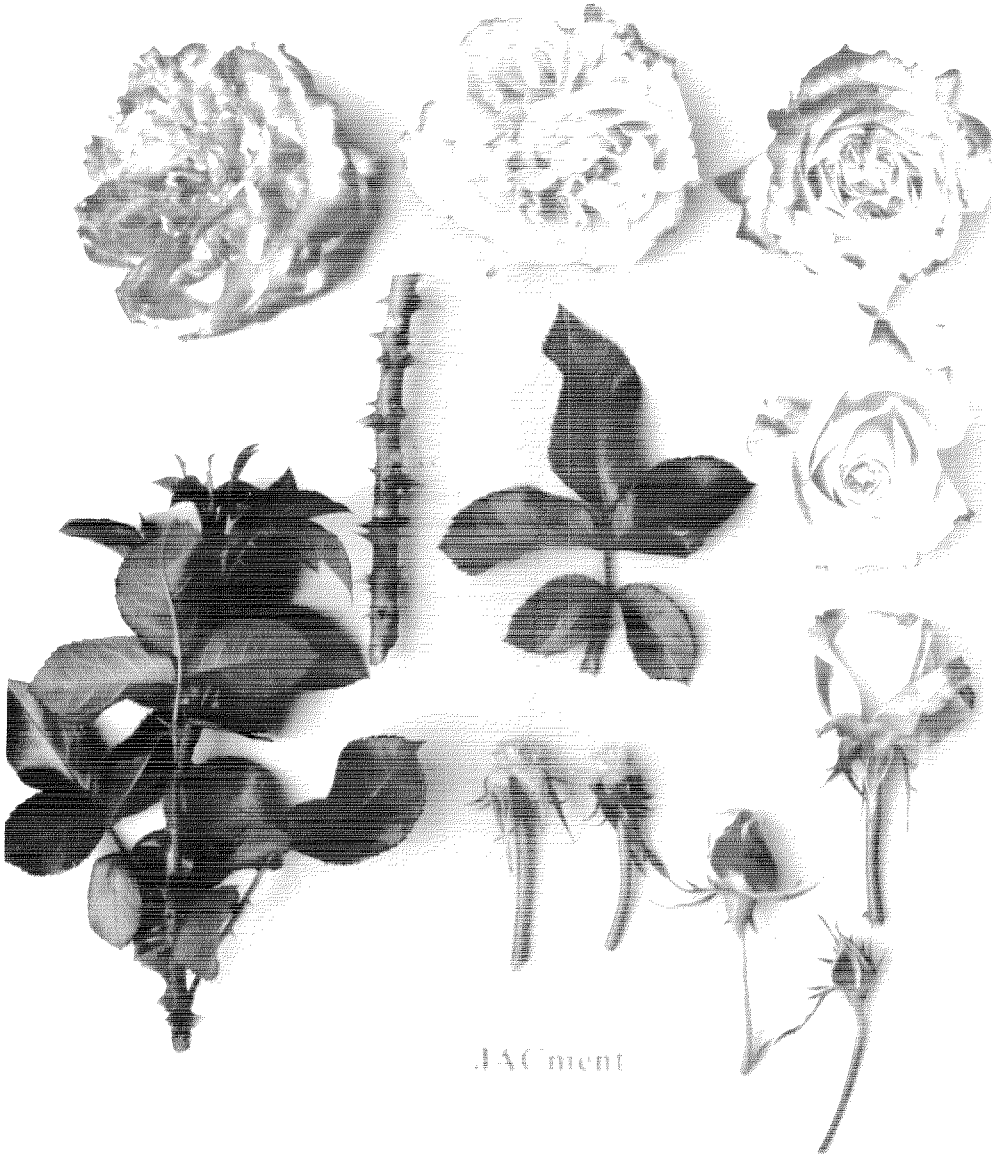
JAC ment